United States Patent

Lin et al.

[11] Patent Number: 6,016,201
[45] Date of Patent: Jan. 18, 2000

[54] INSPECTION METHOD FOR A CORRECTION PATTERN

[75] Inventors: Chin-Lung Lin, Kaohsiung; Yao-Ching Ku, Hsinchu Hsien, both of Taiwan

[73] Assignee: United Microelectronics Corp., Taipei, Taiwan

[21] Appl. No.: 09/135,435

[22] Filed: Aug. 17, 1998

[30] Foreign Application Priority Data

Jun. 11, 1998 [TW] Taiwan .................................. 87109286

[51] Int. Cl.⁷ ..................................................... G01B 11/00
[52] U.S. Cl. ............................. 356/388; 356/384; 356/237
[58] Field of Search ..................................... 356/388, 384, 356/237, 429

[56] References Cited

U.S. PATENT DOCUMENTS 5,546,225  8/1996  Shiraishi ................................. 359/559

*Primary Examiner*—Frank G. Font
*Assistant Examiner*—Reginald A. Ratliff
*Attorney, Agent, or Firm*—Thomas, Kayden, Horstemeyer & Risley

[57] ABSTRACT

An inspection method for a correction pattern includes the following steps. An optical proximity correction is performed to an original pattern to obtain an optical proximity correction pattern. An "exclusive or" logic operation is done to the original pattern and the optical correction pattern to obtain an inspection pattern. The inspection pattern includes a number of kinds of line width sizing. The line width sizing of the inspection pattern is then compared with an optical correction reference size.

6 Claims, 2 Drawing Sheets

⇩ XOR

INSPECTION METHOD FOR A CORRECTION PATTERN

CROSS-REFERENCE TO RELATED APPLICATION

This application claims the priority benefit of Taiwan application Ser. No. 87109286, filed Jun. 11, 1998, the fill disclosure of which is incorporated herein by reference.

BACKGROUND OF THE INVENTION

1. Field of Invention

The present invention relates to an inspection method for correction pattern. More particularly, the present invention relates to an inspection method for comparing the original pattern to the optical proximity correction (OPC).

2. Description of Related Art

Photolithography plays an important role in the semiconductor process. For each semiconductor device, patterns of all films and doping regions are decided by this step. Therefore, the numbers of photolithography required for a process, which is the needed mask number, decide the difficulty of the process.

The photolithography technique is complicate but the principle behind it is fairy simple. For example, photosensitive material is first coated on the wafer. Then, light source is projected to the photosensitive material through the mask, which is mainly composed of glass. The light beam through the mask has the same pattern as the mask so that the mask pattern can be transferred to the photosensitive material on the wafer. The photosensitive material can be, for example, photoresist. Then, after exposure or/and development, equal or complementary pattern on the mask can be transferred to the photosensitive material. If the photosensitive material is positive photoresist, it will obtain an equal pattern as the mask. On the other hand, if the photosensitive is negative photoresist, it will obtain a complementary pattern as the mask.

As negative photoresist is used, after exposure and during the step of development, developer will go in-between the molecular of the negative photoresist. Consequently, the photoresist swells and the differentiation between the after-development pattern of negative photoresist and the mask pattern increases. It is therefore not suitable for process down to 3 µm to use negative photoresist. As a result, positive photoresist is more widely used to the sub-micron semiconductor technique presently.

The exposure technique used for transferring patterns form the mask to the photoresist has three main types: contact type, proximity type and projection type. For the semiconductor technique of deep sub-micron, the degree of precision of the exposure technique is highly limited to photo-resolution. The limitation of photo-resolution may cause error or even failure of pattern transferring. Proximity exposure technique is taken as an example. FIG. 1 illustrates the original mask pattern. After the step of exposure, the pattern of photoresist is substantially the same as the pattern shown in FIG. 2. Comparing the original mask pattern in FIG. 1 and the transferred pattern in FIG. 2, the difference between these two patterns is obvious. For example, the two terminals 10, 12 of the original mask pattern shrinks to becomes terminals 20, 22 after transferred. Also, the configurations of the corners do not correspond with the original pattern but become curved. After exposure, the outer corner 14 shrinks to become a curved shape 24 and the inner corner 16 shrinks to become a curved shape 26.

The problems coming after the error due to pattern transfer is serious. For example, during the back-end processes, the error may cause over-etching and improper coupling of interconnection.

Consequently, during the process of proximity pattern transfer, the original pattern is usually processed through optical proximity correction to form a pattern for transferring. FIG. 3 shows a pattern after optical proximity correction, which has complementary pattern at the shrinking terminals. The complementary pattern at the shrinking terminals is so-called "end-cap". The pattern after optical proximity correction also has complementary pattern at the outer corners and the inner corners. However, the optical proximity correction pattern is a hypothetical pattern, which may also cause improper pattern transfer. Especially nowadays the requirement of precision keeps increasing so even trivial error can influence greatly.

SUMMARY OF THE INVENTION

It is therefore an object of the invention to provide an inspection method of correction pattern, which is able to inspect if the complementary pattern of the correction pattern includes improper sizing. Then, the optical proximity correction pattern is used as a transfer pattern so that the pattern transferred onto the desired region is more precise then the conventional.

According to the invention, an inspection method for a correction pattern including the following steps is disclosed. An optical proximity correction is performed to an original pattern to obtain an optical proximity correction pattern. An "exclusive or" logic operation is done to the original pattern and the optical correction pattern to obtain an inspection pattern. The inspection pattern includes a number of kinds of line width sizing. The line width sizing of the inspection pattern is then compared with an optical correction reference size.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DETAILED DESCRIPTION OF THE INVENTION

During pattern transferring, the original pattern is first processed through optical correction. The pattern after optical correction is then used as a transfer pattern. The precision of the transfer pattern influences greatly the development of the semiconductor subsequent processes.

Figure 1:
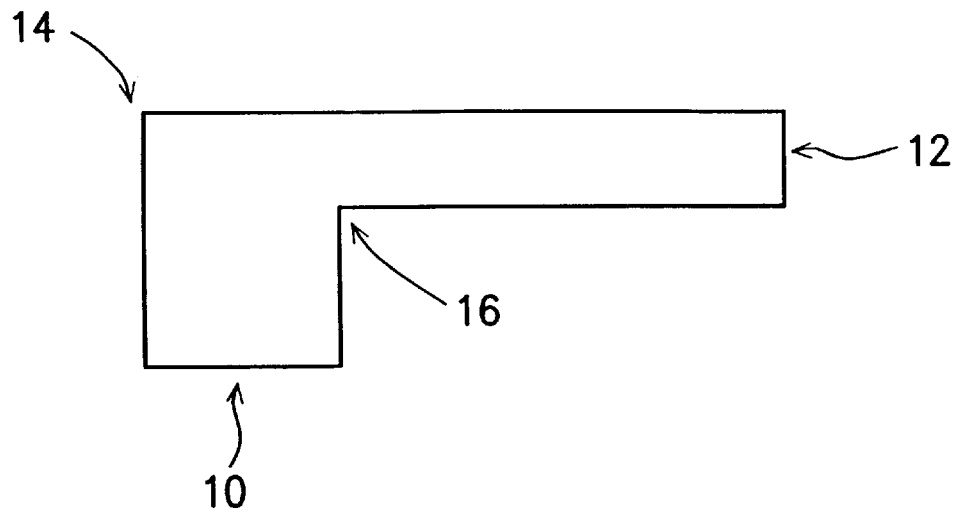
FIG. 1 illustrates a conventional original mask pattern.
Figure 2:
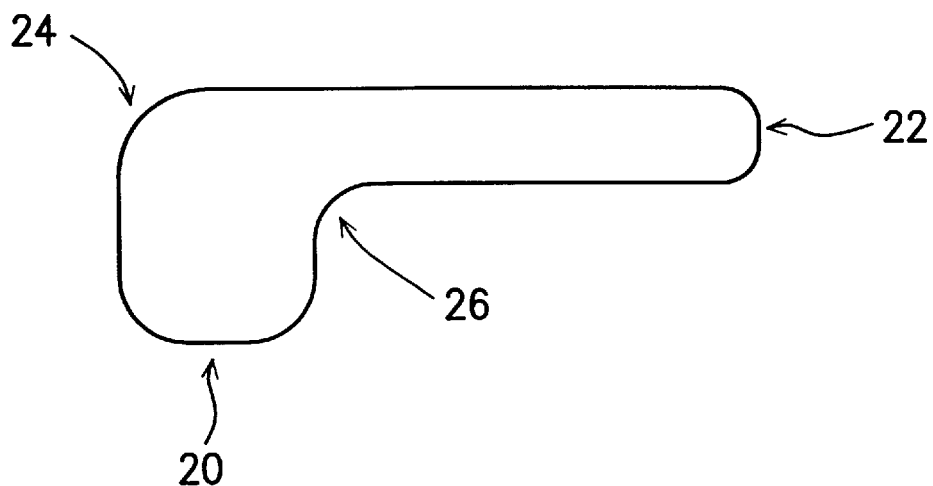
FIG. 2 illustrates a transfer pattern according to FIG. 1.
Figure 3:
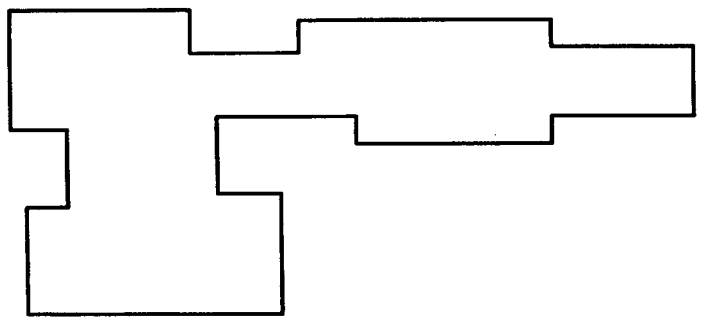
FIG. 3 illustrates an optical proximity correction pattern according to FIG. 1.
Figure 4:
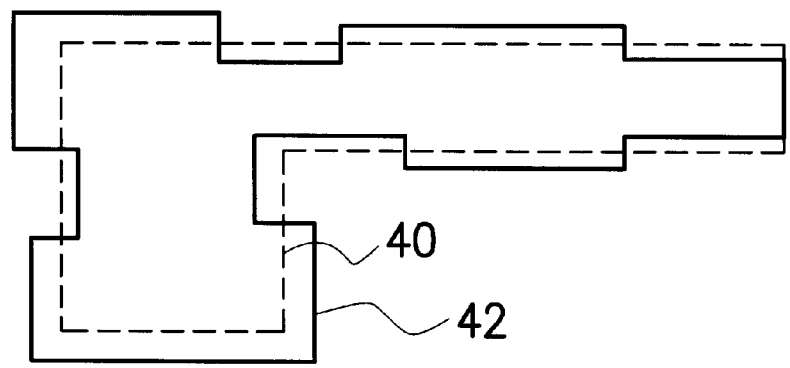
FIG. 4 is a comparative drawing illustrating an original pattern and an optical correction pattern according to a preferred embodiment of the invention.

Referring to FIG. 4 the original pattern 40 is represented by the broken line. On the other hand, taking proximity exposure as an example, the transfer pattern 42 after optical proximity correction is represented by the solid line. Using the original pattern 40 to transferring patterns may cause shrinking terminals and curved corners. As a result, the optical proximity correction pattern 42 but not the original pattern 40 is used as a transfer pattern.

Figure 5:
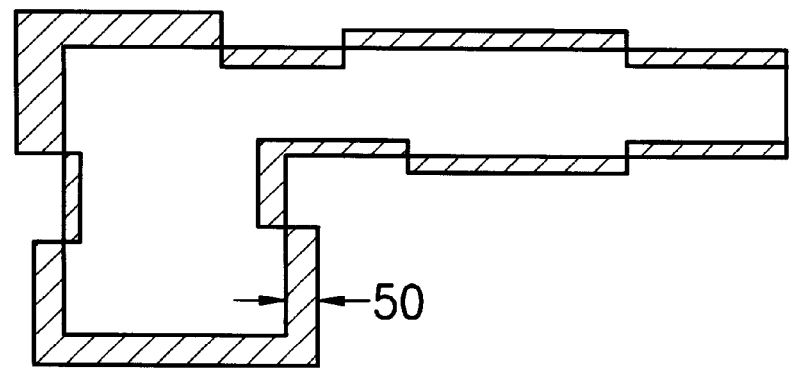
FIG. 5 is an inspection pattern of the original pattern and the optical correction pattern of FIG. 4 after "exclusive or" logical operation.

Next, after an "exclusive or" operation is done to the original pattern 40 and the optical proximity correction pattern 42, an inspection pattern as shown in FIG. 5 is obtained. The inspection pattern has several kinds of line width sizing 50. The line width sizing 50 is then compared with an optical correction reference size to decide whether the optical proximity correction pattern 42 is proper. The optical correction reference size is used as a reference value for the line width sizing of the proximity exposure. If the result coming out shows that the optical proximity correction pattern 42 is improper, further correction is needed for benefiting the subsequent processes.

Therefore, the character of the invention is to inspect the complementary pattern, which is obtained by optical proximity correcting the original pattern, and to decide whether the correction pattern has improper line width sizing. Consequently, the precision for pattern transferring is highly increased.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An inspection method for a correction pattern, which is used to inspect an optical correction pattern of an original pattern, wherein the optical correction pattern is obtained by optical correcting the original pattern, the inspection method comprising:

doing an "exclusive or" logic operation to the original pattern and the optical correction pattern to obtain an inspection pattern, wherein the inspection pattern comprises a plurality of line width sizing; and comparing the line width sizing of the inspection pattern with an optical correction reference size.

2. An inspection method of claim 1, wherein the optical correction pattern is used for proximity exposure.

3. An inspection method of claim 2, wherein the optical correction pattern is an optical proximity correction pattern.

4. An inspection method of claim 2, wherein the optical correction reference size is used as a reference value for the line width sizing of the proximity exposure.

5. An inspection method for a correction pattern, comprising:

performing an optical proximity correction to an original pattern to obtain an optical proximity correction pattern;

doing an "exclusive or" logic operation to the original pattern and the optical correction pattern to obtain an inspection pattern, wherein the inspection pattern comprises a plurality of line width sizing; and comparing the line width sizing of the inspection pattern with an optical correction reference size.

6. An inspection method of claim 5, wherein the optical correction pattern is used for proximity exposure.

* * * * *